United States Patent [19]

Chabala et al.

[11] 4,171,314

[45] Oct. 16, 1979

[54] 13-HALO AND 13-DEOXY C-076 COMPOUNDS

[75] Inventors: John C. Chabala, Westfield; Michael H. Fisher, Bridgewater; Helmut H. Mrozik, Matawan, all of N.J.

[73] Assignee: Merck & Co., Inc., Rahway, N.J.

[21] Appl. No.: 861,810

[22] Filed: Dec. 19, 1977

[51] Int. Cl.$^2$ ............................................. C07D 493/22
[52] U.S. Cl. ............................... 260/343.41; 424/279; 536/17 A
[58] Field of Search ..................................... 260/343.41

[56] References Cited

U.S. PATENT DOCUMENTS 3,950,360    4/1976    Aoki et al. .................... 260/343.41

OTHER PUBLICATIONS

Mishima et al., Tetrahedron Letters 10, pp. 711–714 1975.

Journal of Antibiotics 29(6), Jun. 1976, pp. 76–35 to 76–42 and pp. 76–14 to 76–16.
Derwent Abstract 76268w/46 to Sankyo Co.

*Primary Examiner*—Natalie Trousof
*Assistant Examiner*—Jane T. Fan
*Attorney, Agent, or Firm*—David L. Rose; Harry E. Westlake

[57] ABSTRACT

Derivatives of the C-076 compounds are disclosed wherein the 13-position is unsubstituted or substituted by a halogen atom. The compounds are prepared by removing the glycosyl groups on the 13-position of the C-076 compounds isolated from the fermentation broth of *Streptomyces avermitilis*. This is followed by substitution of the 13-hydroxy group with a halogen, and subsequent removal of the halogen. The disclosed compounds are antiparasitic, anthelmintic, insecticidal and acaracidal agents.

13 Claims, No Drawings

13-HALO AND 13-DEOXY C-076 COMPOUNDS

BACKGROUND OF THE INVENTION

C-076 is a series of macrolides with potent antiparasitic activity. The compounds are isolated from the fermentation broth of *Streptomyces avermitilis* and the morphological characteristics of the microorganism as well as the methods employed to isolate the C-076 compounds are fully described in U.S. patent application Ser. No. 772,601.

Based on taxonomic studies, the microorganisms capable of producing these C-076 compounds are of a new species of the genus Streptomyces, which has been named *Streptomyces avermitilis*. One such culture, isolated from soil is designated MA-4680 in the culture collection of Merck & Co., Inc., Rahway, New Jersey. A C-076 producing sample of this culture has been deposited in the permanent culture collection of the Fermentation Section of the Northern Utilization Research Branch, U.S. Department of Agriculture at Peoria, Illinois, and has been assigned the accession number NRRL 8165. A sample of NRRL 8165 has also been deposited, without-restriction as to availability, in the permanent culture collection of the American Type Culture Collection at 12301 Parklawn Drive, Rockville, Maryland 20852, and has been assigned the accession number ATCC 31,267.

The above microorganism is illustrative of a strain of *Streptomyces avermitilis* which can be employed in the production of the C-076 compounds. However, such description also embraces mutants of the above described microorganism. For example, those C-076 producing mutants which are obtained by natural selection or those producted by mutating agents including X-ray irradiation, ultraviolet irradiation, nitrogen mustard or like treatments are also included within the ambit of this invention.

One example of such an organism is a strain of *Streptomyces avermitilis* MA 4848 which was isolated after irradiation with ultraviolet light of *Streptomyces avermitilis* MA 4680. A lyophilized tube and a frozen vial of this culture has been deposited in the permanent culture collection of the American Type Culture Collection, and they have been assigned the accession numbers 31272 and 31271 respectively. Slightly higher fermentation yields of C-076 have been obtained using this frozen stock as inoculum.

SUMMARY OF THE INVENTION

This invention is concerned with derivatives of the C-076 compounds. Specifically it is concerned with C-076 derivatives which are unsubstituted at the 13-position or substituted by a halogen atom. Thus it is an object of this invention to describe the 13-halo and 13-deoxy compounds of this invention. It is a further object to describe processes for the preparation of such compounds. A still further object is to describe methods and compositions using such compounds as the active ingredient thereof for the treatment of parasitic infections. Further objects will be apparent from a reading of the following description.

DESCRIPTION OF THE INVENTION

The C-076 compounds which are the starting materials for the compounds of this invention are best described in the following structural formula:

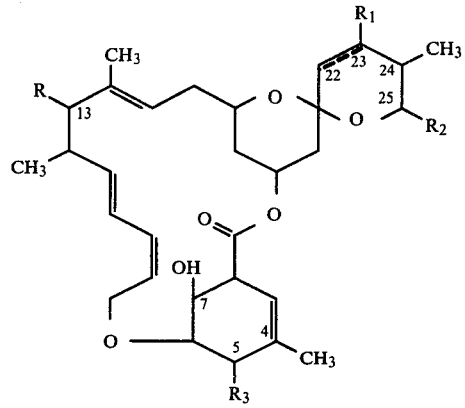

wherein R is the α-L-oleandrosyl-α-L-oleandrosyloxy group of the structure:

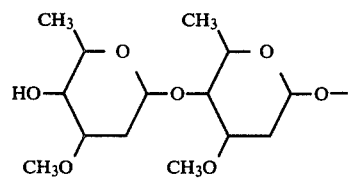

and wherein the broken line indicates a single or a double bond;

$R_1$ is hydroxy and is present only when said broken line indicates a single bond;

$R_2$ is n-propyl or sec- butyl; and $R_3$ is methoxy or hydroxy.

With reference to the foregoing structural formula, the individual C-076 compounds are identified as follows:

| C-076 | $R_1$ | $R_2$ | $R_3$ |
|---|---|---|---|
| A1a | Double bond | sec-butyl | —OCH₃ |
| A1b | Double bond | n-propyl | —OCH₃ |
| A2a | —OH | sec-butyl | —OCH₃ |
| A2b | —OH | n-propyl | —OCH₃ |
| B1a | Double bond | sec-butyl | —OH |
| B1b | Double bond | n-propyl | —OH |
| B2a | —OH | sec-butyl | —OH |
| B2b | —OH | n-propyl | —OH |

The compounds of the instant invention are derived from the above C-076 compounds through a series of compounds commencing with the removal of the α-L-oleandrosyl-α-L-oleandrose side chain at the 13-position. This reaction produces what is identified as the "C-076 aglycone" compounds characterized by having a hydroxy group at the 13-position. The C-076 aglycone compounds are then halogenated with a suitably reactive benzenesulfonyl halide in the presence of a base to produce the "13-deoxy-13-halo-C-076 aglycone" compounds. The halogen is then removed in a reaction with a trialkyltin hydride to produce the "13-deoxy-C-076 aglycone compounds."

Thus, the compounds of the instant invention are realized in the foregoing structural formula wherein R is halogen or hydrogen, and $R_1$, $R_2$ and $R_3$ have the above meanings.

The reaction conditions which are generally applicable to the preparation of C-076 aglycone involve dissolving the C-076 compound in an aqueous non-nucleophilic organic solvent, miscible with water, preferably dioxane, tetrahydrofuran, dimethoxyethane, dimethyl formamide, bis-2-methoxyethyl ether and the like, in which the water concentration is from 0.1 to 20% by volume. Acid is added to the aqueous organic solvent to the extent of 1.0 to 10% by volume. The reaction mixture is generally stirred at about 20°-40° C., preferably at room temperature, for from 6 to 24 hours. The products are isolated, and mixtures are separated by techniques such as column, thin layer, preparative layer and high pressure liquid chromatography, and other known techniques.

The acids which may be employed in the above process include mineral acids and organic acids such as sulfuric, hydrohalic, phosphoric, trifluoroacetic, trifluoromethanesulfonic and the like. The hydrohalic acids are preferably hydrochloric or hydrobromic. The preferred acid in the above process is sulfuric acid.

A further procedure for the preparation of the aglycone compounds is applicable to all of the C-076 compounds, however, it is preferred for use on the compounds which contain a 23-hydroxy group, since some degree of addition to the 22,23-double bond is noticed in those compounds with the 22,23-unsaturation. For the preparation of the aglycone, 1% sulfuric acid, by volume, in methanol at from 20°-40° C., preferably room temperature, for from 6-24 hours has been found to be appropriate.

The other acids listed above may also be employed for this process, at approximately the concentration employed for sulfuric acid.

The above described compounds are isolated from the reaction mixture and mixtures of compounds are separated using techniques known to those skilled in this art, and in particular the chromatographic techniques described above.

The "C-076 aglycone" thus produced is then halogenated to produce the 13-deoxy-13-halo-C-076 aglycone. The halogenation is most readily carried out in the presence of a sufficiently reactive benzenesulfonylhalide compound in the presence of a base. The presence of electron withdrawing substituents on the benzenesulfonylhalide is advantageous and o-nitro substitution is preferred. The reaction is carried out in a non-protic inert solvent such as a halogenated alkyl compound, preferably methylene chloride or chloroform. The reactants are combined slowly at an initial temperature of from −25° to +10° C. to control any initial exothermic reactions, and are maintained at this temperature for up to 2 hours. The reaction temperature is then raised to from about room temperature to the reflux temperature of the reaction mixture for from 10 minutes to 6 hours. It is necessary to carry out the reaction in the presence of a base, preferably an organic amine. It has been found to be preferable to employ the combination of a 4-diloweralkylamino pyridine and trialkylamine. It is most preferred to employ 4-dimethylaminopyridine and diisopropylethylamine as bases for the foregoing reactions. The 13-deoxy-13-halo-C-076 aglycone compounds are isolated by procedures known to those skilled in this art.

In order to avoid unwanted side-reactions, it is important that, in those C-076 compounds with a hydroxy group at the 5-position (the B-series of compounds), and to a lesser extent the 23-hydroxy of the 2-series of compounds, that said hydroxy group be protected. The protecting group is ideally one which may be readily synthesized, will not be affected by the reactions to alter the 13-position substituent, and may be readily removed without affecting any other function of the molecule. One preferred type of protecting group for the C-076 type of molecule is the trisubstituted silyl group, preferably a trialkylsilyl group. One preferred example is the tert-butyldimethylsilyl group. The reaction is carried out by reacting the hydroxy compound with the appropriately substituted silyl halide, preferably the silyl chloride in an aprotic polar solvent such as dimethylformamide. Imidazole is added as a catalyst. The reaction is complete in from ½ to 24 hours at from 0°-25° C. For the 5-position hydroxy group the reaction is complete in about ½ to 3 hours at from 0° C. to room temperature. While the halogenation reaction is much slower at the 23-position hydroxy group (the 2-series of compounds), if it is desired to protect that hydroxy group, the reaction will be complete in about 5 to 24 hours at from about room temperature to 75° C. This reaction is selective to the 5- and 23-positions under the conditions above described, and very little silylation is observed at the 13-position.

The silyl group may be removed after the 13-halogenation or the reaction may be deferred until after the 13-halo group is removed. The silyl group or groups are removed by stirring the silyl compound in methanol containing by a catalytic amount of an acid, preferably a sulfonic acid such as p-toluenesulfonic acid. The reaction is complete in about 1 to 12 hours at from 0° to 50° C.

The 13-deoxy-13-halo-C-076 aglycone which may or may not have the silyl groups protecting the 5-and 23-hydroxy groups is then reduced to form the 13-deoxy-C-076 aglycone. The preferred reducing agent is one that will selectively remove the 13-halo group but will leave the remainder of the molecule untouched. One such reducing agent is a trialkyltinhydride, preferably tributyltinhydride. In addition it is preferable to include in the reaction mixture a free radical initiator since it is believed that the reaction proceeds through a free radical mechanism (not wishing to be bound by theory however, other possible mechanisms are not excluded). Acceptable free radical initiators are varied and include peroxides, such as dibenzoyl peroxides; thiols in the presence of air; azodialkyl nitriles such as azobisisobutyronitrile; ultraviolet light; heat and the like. The reaction conditions will vary depending upon the type of free radical initiator which is employed. For chemical initiators the reaction is complete in about 1 to 6 hours at from 35°-120° C. The preferred reaction temperature is about 85° C. If heat is the initiating agent, higher temperatures are required, about 100°-200° C. for from 1-6 hours. If ultraviolet light is employed, lower temperatures are preferred. Generally the reaction will be complete in from 1-6 hours at −25° to 50° C. in the presence of ultraviolet light. The trialkyltinhydride reaction is generally carried out with no solvent under a blanket of nitrogen or other inert gas. The tin hydride compound is used in excess and becomes the solvent. If desired, however, an inert solvent such as benzene, toluene, xylene and the like could be employed. For obvious reasons, halogenated solvents cannot be employed. The products are isolated using procedures known to those skilled in this art.

The novel 13-halo-and 13-deoxy-C-076 compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesphagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The 13-halo and 13-deoxy-C-076 compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. in cattle, Gastrophilus in horses, and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica.*

The compounds are also useful against insect pests of stored grains such as Tribolium sp., Tenebrio sp. and of agricultural plants such as spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the C-076 derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol, formal and aqueous parenteral formulations are also used. The active 13-halo- or 13-deoxy-C-076 compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection of infestation. Generally good results are obtained with our novel compounds by the oral administration of from about 0.001 to 10 mg. per kg. of animal body weight, such total dose being given at one time or in divided doses over a relatively short period of time such as 1-5 days. With the preferred compounds of the invention, excellent control of such parasites is obtained in animals by administering from about 0.025 to 0.5 mg. per kg. of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active 13-halo- and 13-deoxy-C-076 compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular C-076 derivative employed, the compounds of this invention are usually fed at concentrations of between 0.00001 to 0.002% in the feed in order to achieve the desired antiparasitic result.

In using the compounds of this invention, the individual 13-halo- and 13-deoxy-C-076 components may be prepared and used in that form. Alternatively, mixtures of two or more of the individual monosaccharide and aglycone C-076 components may be used, as well as mixtures of the parent C-076 compounds and the compounds of this invention.

In the isolation of the C-076 compounds, which serve as starting materials for the instant processes, from the fermentation broth, the various C-076 compounds will be found to have been prepared in unequal amounts. In particular an "a" series compound will be prepared in a higher proportion than the corresponding "b" series compound. The weight ratio of "a" series to the corresponding "b" series is about 85:15 to 99:1. The differences between the "a" series and "b" series is constant throughout the C-076 compounds and consists of a sec-butyl group and an n-propyl group respectively at the 25-position. This difference, of course, does not interfere with any of the instant reactions. In particular, it may not be necessary to separate the "b" components from the related "a" component. Separation of these closely related compounds is generally not practiced since the "b" compound is present only in a very small percent by weight, and the structural difference has negligible effect on the reaction processes and biological activities.

The C-076 derivatives of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

The 13-halo- and 13-deoxy-C-076 derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points, however, the chromatographic and analytical methods employed indicate that the compounds are pure.

EXAMPLE 1

23-O-t-Butyldimethylsilyl-C-076-A2a-Aglycone

200 Mg. of C-076-A2a-aglycone in 2.4 ml. of dry dimethylformamide is combined with 133 mg. of imidazole and stirred until all the components are dissolved. 146 Mg. of t-butyldimethylsilylchloride is added and the reaction mixture stirred at room temperature for 24 hours. The reaction mixture is diluted with ether and washed five times with water. The combined water washes are extracted with ether and the combined organic layers washed again with water followed by a single wash with saturated sodium chloride solution. The ether layer is concentrated to dryness in vacuo affording 340 mg. of a gold colored oil. Preparative layer chromatography of the oil on two plates of silica gel eluting with a mixture of 5% tetrahydrofuran and 5% ethanol in methylene chloride affords 113.2 mg. of 23-O-t-butyldimethylsilyl-C-076-A2a-aglycone, the structure of which is confirmed by mass spectrometry, and nuclear magnetic resonance.

EXAMPLE 2

23-O-t-Butyldimethylsilyl-13-Chloro-13-deoxy-C-076-A2a-Aglycone

20 Mg. of 23-O-t-butyldimethylsilyl-C-076-A2a-aglycone is combined with 0.7 ml. of a methylene chloride solution containing 15 mg. of 4-dimethylaminopyridine and 0.021 ml. (15.5 mg.) of diisopropylethylamine. The mixture is cooled in an ice bath and a solution of 0.1 ml. of methylene chloride containing 20 mg. of o-nitrobenzenesulfonylchloride is added dropwise. The reaction mixture is stirred for 45 minutes in an ice bath and then for 3 hours at room temperature. Ice chips are added to the reaction mixture and stirred. When the ice is melted, ether is added to the mixture and the layers separated. The aqueous layer is again extracted with ether and the combined organic layers washed twice with water, dried over magnesium sulfate and evaporated to dryness under a stream of nitrogen affording 35 mg. of a gold film. Preparative layer chromatography of the material on a single silica gel plate eluting with 5% tetrahydrofuran and 5% ethanol in methylene chloride affords 10.1 mg. of 23-O-t-butyldimethylsilyl-13-chloro-13-deoxy-C-076-A2a-aglycone, the structure of which is confirmed by mass spectrometry and 300 MHz nuclear magnetic resonance.

EXAMPLE 3

13-Chloro-13-Deoxy-C-076-A2a-Aglycone

A solution of 10 mg. of 23-O-t-butyldimethylsilyl-13-deoxy-C-076-A2a-aglycone in 1.0 ml. of methanol containing 1% p-toluenesulfonic acid dihydrate is stirred at room temperature for 5 hours. The reaction mixture is diluted with 25 ml. of ethyl acetate, and washed with aqueous sodium bicarbonate and water. The organic layer is dried and evaporated to dryness in vacuo affording 13-chloro-13-deoxy-C-076-A2a-aglycone.

EXAMPLE 4

13-Chloro-13-Deoxy-C-076-A2a-Aglycone

20 Mg. of C-076-A2a-aglycone is dissolved in 0.7 ml. of methylene chloride containing 16 mg. of dimethylaminopyridine and 16.8 mg. (0.023 ml.) of 4-diisopropylethylamine. The reaction mixture is cooled in an ice bath and 0.1 ml. of methylene chloride containing 21.5 mg. of o-nitrobenzenesulfonylchloride is added dropwise. The reaction mixture is stirred in an ice bath for 1 hour and allowed to warm to room temperature and stirred for 4 hours. Ice is added and stirred until melted. Ether is added and the layers shaken and separated. The aqueous layer is extracted with ether and the organic layers combined, washed three times with water, dried over magnesium sulfate and evaporated to dryness under a stream of nitrogen affording 40 mg. of a brown film. Preparative layer chromatography on silica gel plates eluting with 3% tetrahydrofuran and 1% ethanol in methylene chloride affords 4.7 mg. of 13-chloro-13-deoxy-C-076-A2a-aglycone which is identified by a nuclear magnetic resonance and mass spectrometry.

EXAMPLE 5

13-Deoxy-C-076-A2a-Aglycone

80 Mg. of 13-chloro-13-deoxy-C-076-A2a-aglycone is dissolved in 1.5 ml. of tributyltinhydride and 20 mg. of azobisisobutylronitrile is added. The reaction mixture is heated under nitrogen at 85° C. for 3½ hours. The reaction mixture is cooled and placed on a silica gel preparative layer chromatography plate and eluted with chloroform affording 110 mg. of a glass. Repeated preparative layer chromatography on silica gel using methylene chloride with 2% tetrahydrofuran and 0.07% ethanol as eluent affords 10 mg. of a white glass which is identified by mass spectrometry and 300 MHz nuclear magnetic resonance as 13-deoxy-C-076-A2a-aglycone.

EXAMPLE 6

13-Deoxy-23-O-t-Butyldimethylsilyl-C-076-A2a-Aglycone

1 Mg. of 13-chloro-13-deoxy-23-O-t-butyldimethylsilyl-C-076-A2a-aglycone is dissolved in 50 microliters of toluene and 100 microliters of tributyltinhydride and 200 micrograms of azobisisobutyronitrile and heated at 60° C. for 4 hours. The product is isolated by direct chromatography on a preparative layer silica gel chromatography plate eluting with 1.5% tetrahydrofuran in chloroform affording 13-deoxy 23-O-t-butyldimethylsilyl-C-076-A2a-aglycone which is identified by mass spectrometry.

EXAMPLE 7

13-Deoxy-C-076-A2a-Aglycone

Following the procedure of Example 3 using 13-deoxy-23-O-t-butyldimethylsilyl-C-076-A2a-aglycone in place of 23-O-t-butyldimethylsilyl-13-chloro-13-deoxy-C-076-A2a-aglycone, there is obtained 13-deoxy-C-076-A2a-aglycone.

EXAMPLE 8

5-O-t-Butyldimethylsilyl-C-076-B1a-Aglycone

100 Mg. of C-076-B1a-aglycone is dissolved in 1.2 ml. of anhydrous dimethylformamide and 46 mg. of imidazole is added followed by 50 mg of t-butyldimethylsilylchloride. The reaction is maintained at 20° C. for 30 minutes and diluted with ether. The mixture is washed with water, dried and concentrated in vacuo to a colorless glass. Further purification on a preparative layer chromatography plate eluting with a methylene chloride, tetrahydrofuran mixture affords purified 5-O-t-butyldimethylsilyl-C-076-B1a-aglycone.

Following the above procedure, utilizing C-076 B2a aglycone in place of C-076 B1a aglycone, affords 5-O-t-butyldimethylsilyl-C-076-B2a-aglycone.

EXAMPLE 9

5-O-t-Butyldimethylsilyl-13-Deoxy-13-chloro-C-076-B1a-Aglycone

Following the procedure of Example 2 utilizing 5-O-t-butyldimethylsilyl-C-076-B1a-aglycone in place of 23-O-t-butyldimethylsilyl-C-076-A2a-aglycone, there is produced 5O-t-butyldimethylsilyl-13-deoxy-13-chloro-C-076 B1a-aglycone.

Following the above referenced procedure using 5-O-t-butyldimethylsilyl-C-076-B2a-aglycone in place of 5-O-t-butyldimethylsilyl-C-076-B1a-aglycone, there is obtained 5-O-t-butyldimethylsilyl-13-deoxy-13-chloro-C-076-B2a-aglycone.

EXAMPLE 10

5-O-t-Butyldimethylsilyl-13-Deoxy-C-076-B1a-Aglycone

Following the procedure of Example 5 utilizing 5-O-t-butyldimethylsilyl-13-deoxy-13-chloro-C-076-B1a-aglycone in place of 13-chloro-13-deoxy-C-076-A2a-aglycone, there is produced, 5-O-t-butyldimethylsilyl-13-deoxy-C-076-B1a-aglycone.

Following the above referenced procedure using 5-O-t-butyldimethylsilyl-13-deoxy-13-chloro-C-076-B2a in place of 5-O-t-butyldimethylsilyl-13-deoxy-13-chloro-C-076-B1a-aglycone, there is produced 5-O-t-butyldimethylsilyl-13-deoxy-C-076-B2a-aglycone.

EXAMPLE 11

13-Deoxy-C-076-B1a-Aglycone

A solution of 13 mg. of 5-O-t-butyldimethylsilyl-13-deoxy-C-076-B1a-aglycone in 1.0 ml. of methanol containing 1% p-toluenesulfonic acid dihydrate is stirred at 20° C. for 3 hours. The reaction is diluted with 30 ml. of ethyl acetate, washed with aqueous sodium bicarbonate solution and then with water. The organic layer is dried and evaporated to dryness in vacuo to afford 13-deoxy-C-076-B1a-aglycone as a clear glass.

Following the above procedure, utilizing 5-O-t-butyldimethylsilyl-13-deoxy-C-076-B2a-aglycone in place of 5-O-t-butyldimethylsilyl-13-deoxy-C-076-aglycone, there is obtained 13-deoxy-C-076-B1a-aglycone.

If the products of Example 9 are hydrolyzed according to the foregoing procedure, there will be obtained 13-chloro-13-deoxy-C-076-B1a-aglycone and 13-chloro-13-deoxy-C-076-B2a-aglycone.

EXAMPLE 12

13-Chloro-13-Deoxy-C-076-A1a-Aglycone

Following the procedure of Example 4, employing C-076 A1a-aglycone in place of C-076 A2a-aglycone, there is produced 13-chloro-13-deoxy-C-076-A1a-aglycone.

EXAMPLE 13

13-Deoxy-C-076-A1a-Aglycone

Following the procedure of Example 5, employing 13-chloro-13-deoxy-C-076-A1a-aglycone in place of 13-chloro-13-deoxy-C-076-A2a-aglycone, there is produced 13-deoxy-C-076-A1a-aglycone.

PREPARATION 1

A 250 ml. baffled Erlenmeyer flask containing 50 ml. of the following medium:

| | |
|---|---|
| Lactose | 2.0% |
| Distiller's solubles | 1.5% |
| Autolyzed yeast, Ardamine pH | 0.5% |
| pH - before sterilization | 7.0 | is inoculated with the contents of one frozen vial of *Streptomyces avermitilis* MA 4848 and incubated on a rotary shaker at 28° C. for 24 hours at 150 RPM.

10 Ml. of the above fermentation media is employed to inoculate 500 ml. of the same medium as above in a 2 liter baffled Erlenmeyer flask. The fermentation media is incubated at 150 RPM on a rotary shaker at 28° C. for 24 hours.

All of the foregoing media is employed to inoculate 467 liters of the following media in a 756 liter stainless steel fermentor:

| | |
|---|---|
| Lactose | 2.0% |
| Distiller's solubles | 1.5% |
| Autolyzed yeast, Ardamine pH | 0.5% |
| Polyglycol 2000 | 0.32 ml./liter |
| pH - before sterilization | 7.0 |

The fermentation media is incubated at 28° C. for 40 hours with an air flow 10 cubic feet per minute and an agitation rate 130 RPM.

230 Liters of the above media is employed to inoculate 4,310 liters of the following medium in a 5,670 liter stainless steel fermentor:

| | |
|---|---|
| Dextrose | 4.5% |
| Peptonized milk | 2.4% |
| Autolyzed yeast, Ardamine pH | 0.25% |
| Polyglycol 2000 | 2.5 ml./liter |
| pH - before sterilization | 7.0 |

The fermentation continues for 144 hours at 26° C. with an air flow rate of 54.3 cubic feet per minute and agitation of 120 RPM.

The fermentation media are filtered and the mycelial filter cake washed with about 550 liters of water, the filtrate and washings are discarded. The filter cake is agitated with about 1500 liters of acetone for about one hour and filtered. The filter cake is washed with a mixture of about 150 liters of acetone and 40 liters of deionized water affording about 2000 liters of extract.

The foregoing fermentation and extraction is repeated on the same scale affording a further 2000 liters of acetone extract which is combined with the first extract and evaporated to a volume of about 800 liters. The pH of the concentrate is adjusted to about 4.7 with concentrated hydrochloric acid and combined with about 800 liters of methylene chloride. The combined solvents are agitated for about 4 hours and separated. The aqueous layer is combined with an additional 800 liters of methylene chloride and agitated for about 4 hours. The layers are separated and each methylene chloride extract separately treated with about 10 kilograms of Super-Cel and filtered. Both extracts are evaporated to a combined volume of about 60 liters.

PREPARATION 2

The 60 liter solution of C-076 in methylene chloride of the previous example is concentrated to dryness in vacuo and the residue is combined 3 times with 60 liter portions of methanol and evaporated to dryness to remove any residual methylene chloride. The final methanol concentrate volume is approximately 36 liters. The methanol solution is stored overnight and filtered. The filter cake is washed with 40 liters of fresh methanol and the methanol filtrates and washings are combined. The methanol solution is combined with 95 liters of ethylene glycol and 130 liters and heptane. The 2 layer solution is agitated for 5 minutes and the lower layer (ethylene glycol and methanol) is separated. The heptane solution is washed with a mixture of 20 liters of ethylene glycol and 6.3 liters methanol. After five minutes of agitation, the lower layer is separated and combined with the first ethylene glycol/methanol extract. An equal volume of water (approximately 150 liters) containing 79 g. of salt per liter is added to the ethylene glycol/methanol extracts. This solution is extracted with 150 liters of ethyl ether with agitation for 5 minutes. The ether layer is washed with 75 liters of water ($\frac{1}{2}$ volume) and agitated for 5 minutes and the layers separated. This procedure is repeated an additional 2 times (the final water wash contains 20 g. of salt per liter) affording a final ether layer volume of 110 liters. The ether layer is concentrated in vacuo, to a minimum volume, keeping the temperature less than 25° C. 40 liters of methylene chloride is added to the residue and the solution is evaporated to dryness. This procedure is repeated and the final residue concentrated in vacuo at 50° C. to dryness.

PREPARATION 3

A 30 centimeter diameter column is prepared with a layer of 34 kilograms of activated alumina followed by a layer of 34 kilograms of activated carbon in a solution of methylene chloride. The residue from the previous example is dissolved in methylene chloride to a volume of 34 liters and applied to the column and eluted with 34 liters of methylene chloride. these fractions are discarded. A 3% solution of isopropanol and methylene chloride (20.8 liters of isopropanol and 660 liters of methylene chloride) is applied to the column and eluted in approximately 200 liter fractions. The combined isopropanol and methylene chloride fractions are evaporated in vacuo at a bath temperature of about 60° C. to a volume of about 20 liters. The bath temperature is reduced to about 45° C. and the extract is evaporated to dryness in vacuo. The residue is dissolved in 10 parts methylene chloride, 10 parts hexane and one part methanol to a final volume of 15 liters. This solution is applied directly to the Sephadex LH-20 column of the next example.

PREPARATION 4

A 30 centimeter diameter column is prepared in methanol with 36 kilograms of Sephadex LH-20 (available from Pharmacia Fine Chemicals, 800 Centennial Avenue, Piscataway, New Jersey 08854) and washed with a solvent consisting of 10 parts methylene chloride, 10 parts hexane and one part methanol. One-fourth of the C-076 solution of Example 3 is applied to the column and the column eluted at a rate of 250 ml. per minute. Two 20 liter forecuts are collected and discarded followed by 20 two liter rich cuts (identified as fractions 1-20), followed by a single 20 liter tail cut, which is discarded. Fractions 1-8 are found to contain the C-076 A compounds and fractions 9-20 are found to contain the C-076 B compounds.

PREPARATION 5

The process of Preparation 4 is repeated on the same scale three more times and all of the fractions containing the C-076 B components (fractions 9-20) are combined and evaporated to dryness, affording 818 g. of crude mixed C-076 B components. The sample is found to contain 55% C-076 B1 and 39% of C-076 B2. 680.5 G. of this sample is dissolved in 2 liters of methylene chloride and placed in a 22 liter three neck round bottom flask followed by the addition of 13.6 liters of methanol. The methylene chloride is removed by distillation. 13.6 Liters of ethylene glycol is added as the methanol is being distilled under reduced pressure. The rate of distillation is maintained such that the temperature of the solution did not go below 65° C. When the addition of the ethylene glycol is complete, the solution is allowed to cool at 5° C. for sixteen hours. The crystals are filtered and washed with 1 liter of cold ethylene glycol. The crystals are then redissolved in 2 liters of methylene chloride the solution placed in a 22 liter three necked round bottom flask. The procedure described above is repeated twice. The first time 12.5 liters each of methanol and ethylene glycol is employed and the second time 13.6 liters each of methanol and ethylene glycol is employed. The final crystals are washed with 1 liter of cold ethylene glycol and 1 liter of water. The crystals are dissolved in 4 liters of water and dried by filtering through sodium sulfate. The benzene solution is concentrated to a volume of 2 liters and lyophilized affording 241.2 gm. of a white powder consisting of 98% C-076 $B_1$ and 1% of C-076 $B_2$.

The mother liquors (22 liters) from the first two crystallizations above are combined and diluted with 22 liters of water. The aqueous solution is extracted with 60 liters of toluene and again with 15 liters of toluene. The toluene extract is then washed with 48 liters of water. The organic phase is filtered through Super-Cel to remove any residual water and evaporated affording 336 gm. of solid material consisting of 79% C-076 $B_2$ and 16% C-076 $B_1$ compounds.

PREPARATION 6

In the four Sephadex LH-20 columns of the procedure of Preparation 4, fractions 1-8 contain the C-076 A compounds and are combined. By HPLC analysis the mixture is found to contain 252 g. of C-076 A2a, 16 g. of A2b, 94 g. of A1a and 24 g. of A1b. The material is dissolved in a solvent system consisting of hexane:toluene:methanol in the proportion of 6:1:1 and applied to the Sephadex LH-20 column of the same dimensions as the one used in Preparation 4 in the above solvent. Fractions are collected at the rate of 250 ml. per minute and a 20 liter forecut is collected and discarded. Further elution affords 2 additional 20 liter forecuts which are also discarded and 50 four liter rich cuts which contain C-076 A compounds. Fractions 3-8 are found to contain predominately C-076 A1 components (40.2 g. A1a and 6.7 g. A1b), and fractions 29-36 are found to contain C-076 A2 compounds (117.2 g. A2a and 7.35 g. of A2b). Fractions 9-28 contain a mixture of C-076 A1 and A2 compounds.

PREPARATION 7

A sample of 150 g. of C-076 B1 from Preparation 5 is dissolved in 3 liters of a solvent mixture of hexane:toluene:methanol in the ratio of 3:1:1. The solution is passed through a column of Sephadex LH-20 (of the same dimensions as the one used in Preparation 4) in the above solvent taking fractions at the rate of 250 ml. per minutes. After two 20 liter portions of the solvent mixture are collected and discarded, forecut of 10 liters is taken and discarded. Then 30 richcuts of 2 liters each are taken. Fractions 1-13 and 25-30 are discarded. Fractions 14-16 are combined and contain 80 g. of predominately C-076 B1a. Fractions 22-24 are combined and contain 6.7 g. of predominately C-076 B1b. Fractions 17-21 contain a mixture of C-076 B1a and B1b.

Fractions 17-21 above are combined and concentrated and passed through a Sephadex LH-20 column with the same solvent system as above. Three 20 liter forecuts are taken and discarded. Richcuts are then taken as follows: 5 cuts of 2 liters each (fractions 1-5); 20 cuts of 1 liter each (fractions 6-25); and 10 cuts of 2 liters each (fractions 26-35). Fractions 1-15 are discarded; fractions 16-21 contain 13.5 g. of C-076 B1a and 0.4 g. of C-076 B1b; fractions 22-26 contain 44 g. of C-076 B1a and 0.13 g. of C-076 B1b; fractions 27-30 contain 10.2 g. of C-076 B1a and 0.8 g. of C-076 B1b.

PREPARATION 8

A mixture of all 8 C-076 components are chromatographed on a high pressure liquid chromatography column 4 mm. × 30 cm. packed with 10 micron $\mu$ Bondapak $C_{18}$ silica gel (available from Waters Associates Inc., Maple Street, Milford, Massachusetts 01757) eluting with 85:15 (v/v) methanol:water at a constant 40° C. At a flow rate of 1.2 ml. per minute all eight compounds are separated and the elution volumes, which under the foregoing constant conditions are characteristic of the individual compounds are as follows:

|  | Elution Volume (Ve) Ml |
| --- | --- |
| C-076 $B_2$b | 5.90 |
| C-076 $B_2$a | 6.52 |
| C-076 $A_2$b | 7.12 |
| C-076 $A_2$a | 7.88 |
| C-076 $B_1$b | 8.36 |
| C-076 $B_1$a | 9.60 |
| C-076 $A_1$b | 10.24 |
| C-076 $A_1$a | 11.88 |

The separation of C-076 "b" components from the respective "a" components is accomplished using techniques such as high pressure liquid chromatography. An absolute methanol solution of 30 microliters of a mixture of C-076 A1a and A1b, estimated to contain 30 micrograms of C-076 A1b is placed on a 3×250 mm. high pressure liquid chromatography column containing Spherisorb 5 micron ODS (available from Spectra Physics) as packing. The column is eluted with 85:15 methanol-water at a rate of 0.15 ml./min. The elution of the products are followed by observing the ultraviolet absorption of the eluent and collecting the individual components at the outlet of the UV monitor. 30 Micrograms of C-076 A1b is recovered in this manner.

What is claimed is:

1. A compound having the formula:

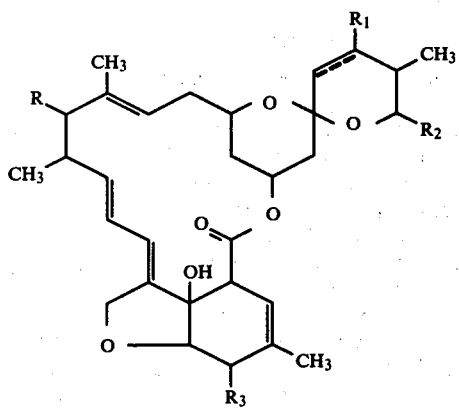

wherein the broken line indicates a single or a double bond;

R is halogen or hydrogen;

$R_1$ is hydroxy and is present only when said broken line indicates a single bond;

$R_2$ is n-propyl or sec-butyl; and $R_3$ is methoxy or hydroxy.

2. The compound of claim 1 wherein $R_2$ is n-propyl.

3. The compound of claim 1 wherein $R_2$ is sec-butyl.

4. The compound of claim 3 wherein R is hydrogen.

5. The compound of claim 4 wherein R is hydrogen; $R_1$ is a 22,23 double bond; $R_2$ is sec-butyl; and $R_3$ is methoxy, which is 13-deoxy C-076 A1a-aglycone.

6. The compound of claim 4 wherein R is hydrogen; $R_1$ is hydroxy; $R_2$ is sec-butyl; and $R_3$ is methoxy which is 13-deoxy C-076 A2a-aglycone.

7. The compound of claim 4 wherein R is hydrogen; $R_1$ is a 22,23 double bond; $R_2$ is sec-butyl; and $R_3$ is hydroxy, which is 13-deoxy C-076 B1a-aglycone.

8. The compound of claim 4 wherein R is hydrogen; $R_1$ is hydroxy; $R_2$ is sec-butyl; and $R_3$ is hydroxy, which is 13-deoxy C-076 B2a-aglycone.

9. The compound of claim 3 wherein R is chlorine.

10. The compound of claim 9 wherein R is chlorine; $R_1$ is a 22,23-double bond; $R_2$ is sec-butyl; and $R_3$ is methoxy, which is 13-chloro-13-deoxy-C-076 A1a-aglycone.

11. The compound of claim 9 wherein R is chlorine; $R_1$ is hydroxy; $R_2$ is sec-butyl; and $R_3$ is methoxy, which is 13-chloro-13-deoxy-C-076-A2a-aglycone.

12. The compound of claim 9 wherein R is chlorine; $R_1$ is a 22,23 double bond; $R_2$ is sec-butyl; and $R_3$ is hydroxy, which is 13-chloro-13-deoxy-C-076-B1a-aglycone.

13. The compound of claim 9 wherein R is chlorine; $R_1$ is hydroxy; $R_2$ is sec-butyl; and $R_3$ is hydroxy, which is 13-chloro-13-deoxy-C-076-B2a-aglycone.

* * * * *